United States Patent [19]

Miller

[11] Patent Number: 5,558,851
[45] Date of Patent: Sep. 24, 1996

[54] PREPARATION OF ALUMINOSILICATE ZEOLITES

[75] Inventor: Stephen J. Miller, San Francisco, Calif.

[73] Assignee: Chevron U.S.A. Inc., San Francisco, Calif.

[21] Appl. No.: 309,216

[22] Filed: Sep. 20, 1994

Related U.S. Application Data

[63] Continuation-in-part of Ser. No. 141,142, Oct. 21, 1993, abandoned, which is a continuation-in-part of Ser. No. 991,872, Dec. 16, 1992.

[51] Int. Cl.$^6$ .......................... C01B 39/04; C01B 39/38; C01B 39/42
[52] U.S. Cl. .................. 423/702; 423/705; 423/706; 423/707; 423/708; 423/716; 423/DIG. 22; 423/DIG. 27; 423/DIG. 33; 423/DIG. 36; 502/66; 502/71; 502/74; 502/77
[58] Field of Search .................... 423/700, 702, 423/704, 705, 706, 707, 708, 716; 502/66, 70, 71, 74, 77

[56] References Cited

U.S. PATENT DOCUMENTS

| | | |
|---|---|---|
| 3,702,886 | 11/1972 | Argauer . |
| 4,091,007 | 5/1978 | Dwyer et al. . |
| 4,522,705 | 6/1985 | Chu et al. ............................. 208/111 |
| 4,560,542 | 12/1985 | Robson ................................. 502/60 |
| 4,585,639 | 4/1986 | Szostak ................................. 502/62 |
| 5,145,659 | 9/1992 | McWilliams .......................... 502/63 |
| 5,240,892 | 8/1993 | Klocke ................................. 502/77 |
| 5,252,527 | 10/1993 | Zones ................................... 502/64 |
| 5,254,514 | 10/1993 | Nakagawa ............................. 502/62 |
| 5,277,791 | 1/1994 | DiRenzo ................................ 208/46 |
| 5,460,796 | 10/1995 | Verdunn et al. ....................... 423/700 |
| 5,486,348 | 1/1996 | Verdunn et al. ....................... 423/700 |

FOREIGN PATENT DOCUMENTS

| | | |
|---|---|---|
| 0156595 | 5/1985 | European Pat. Off. . |
| 2097416 | 4/1990 | Japan . |

OTHER PUBLICATIONS

"Microporous Materials" –Jan. 1994 Elsevier Science B. V. –R. Althoff et al., pp. 557–562.
Aiello et al., *Zeolite Crystallization From Dense Systems*, Materials Engineering, vol. 3 #3 pp. 407–416, 1992.
Wenyang et al. "Jonaqueous Synthesis of ZSM–35 and ZSM–5" *Zeolites*, Nov. 1989, vol. 9, pp. 468–473.
Jianquan et al, "Zeolite ZSM–35 Synthesized by 'Kneading' Method in a Nonaqueous System" J. Chem Soc. Chem Commun., 1993 pp. 659–60.

*Primary Examiner*—Mark L. Bell
*Assistant Examiner*—David Sample
*Attorney, Agent, or Firm*—W. K. Turner; A. W. Klaassen; R. J. Sheridan

[57] ABSTRACT

A method is disclosed for preparing a crystalline aluminosilicate zeolite from a reaction mixture containing only sufficient water so that the reaction mixture may be shaped if desired. In the method, the reaction mixture is heated at crystallization conditions and in the absence of an external liquid phase, so that excess liquid need not be removed from the crystallized material prior to drying the crystals.

52 Claims, No Drawings

PREPARATION OF ALUMINOSILICATE ZEOLITES

CROSS REFERENCE TO RELATED APPLICATION

This application is a continuation-in-part of application Ser. No. 08/141,142, filed Oct. 21, 1993, now abandoned, which is a continuation-in-part of application Ser. No. 07/991,872, filed Dec. 16, 1992.

FIELD OF THE INVENTION

The present invention relates to a process for producing a crystalline aluminosilicate zeolite from a reaction mixture which contains only sufficient water to form the reaction mixture into a desired shape.

BACKGROUND

Molecular sieves are a commercially important class of crystalline materials. They have distinct crystal structures with ordered pore structures which are demonstrated by distinct X-ray diffraction patterns. The crystal structure defines cavities and pores which are characteristic of the different species. Natural and synthetic crystalline molecular sieves are useful as catalysts and adsorbents. The adsorptive and catalytic properties of each molecular sieve are determined in part by the dimensions of its pores and cavities. Thus, the utility of a particular molecular sieve in a particular application depends at least partly on its crystal structure. Because of their unique sieving characteristics, as well as their catalytic properties, molecular sieves are especially useful in such applications as gas drying and separation and hydrocarbon conversion. The term "molecular sieve" refers to a material prepared according to the present invention a fixed, open-network structure, usually crystalline, that may be used to separate hydrocarbons or other mixtures by selective occlusion of one or more of the constituents, or may be used as a catalyst in a catalytic conversion process.

Prior art methods of preparing crystalline zeolites typically produce finely divided crystals which must be separated from an excess of liquid in which the zeolite is crystallized. The liquid, in turn, must be treated for reuse or else be discarded, with potentially deleterious environmental consequences. Preparing commercially useful catalytic materials which contain the powdered zeolite also normally requires additional binding and forming steps. Typically, the zeolite powder as crystallized must be mixed with a binder material and then formed into shaped particles or agglomerates, using methods such as extruding, agglomeration, spray drying, and the like. These binding and forming steps greatly increase the complexity of catalyst manufacture involving zeolitic materials. The additional steps may also have an adverse effect on the catalytic performance of the zeolite so bound and formed.

Crystalline zeolites may be divided into two general types based on crystal structure considerations. One type includes zeolites having a $SiO_2/Al_2O_3$ molar ratio in the crystalline lattice typically less than 12, which are conventionally prepared without an organic templating agent. Many of these zeolites also contain sodalite substructures, and have a tetrahedral atom density of less than about 15 $TO_2/1000$ $Å^3$. Zeolites having these general characteristics include, for example, zeolites A, N-A, ZK-4, faujasite, X, Y, ZK-5 and rho.

A number of processes have been offered for preparing crystalline zeolites of this type within discrete particles. For example, Howell, et al., in U.S. Pat. No. 3,119,660 teaches a method for producing crystalline metal aluminosilicate zeolite by reacting preformed bodies of clay particles in an aqueous reactant mixture including alkali metal oxide. Similar processes for preparing zeolites from formed bodies, which may contain zeolitic seed crystals, in alkali solutions are also taught in U.S. Pat. No. 4,424,144 to Pryor, et al., U.S. Pat. No. 4,235,753 to Brown, et al., U.S. Pat. No. 3,777,006 to Rundell, et al., U.S. Pat. No. 3,119,659 to Taggart, et al, U.S. Patent No. 3,773,690 to Heinze, et al., U.S. Patent No 4,977,120 to Sakurada, et al and GB 2 160 517 A. U.S. Patent No. 3,094,383 teaches a method of forming an A type zeolite by aging a homogeneous reaction mixture out of contact with an external aqueous liquid phase but under conditions to prevent the dehydration of the mixture. GB 1 567 856 discloses a method of preparing zeolite A by heating an extruded mixture of metakaolin powder and sodium hydroxide.

In U.S. Pat. No. 4,058,586, Chi, et al. discloses a method for crystallizing zeolites within formed particles containing added powdered zeolite, where the formed particles furnish all of the liquid needed for crystallization. Crystallizing the particles in an aqueous alkaline solution is not required using the process of Chi, et al.

Verduijn, in WO 92/12928, teaches a method of preparing binder-free zeolite aggregates by aging silica-bound extruded zeolites in an aqueous ionic solution containing hydroxy ions. According to the disclosure of Verduijn, the presence of zeolite crystals in the extrudate is critical for making strong crystalline zeolite extrudates. Verduijn, et al., in EPO A1/0,284,206, describe a method of preparing binderless zeolite L by forming silica and preferably 10–50 wt % preformed zeolite L crystallites into particles, and then reacting the particles with an alkaline solution containing a source of alumina to form the zeolite L. More recently, similar methods have been proposed for preparing high silica zeolitic materials. Conventional methods for preparing high silica materials, having a $SiO_2/Al_2O_3$ molar ratio of greater than about 10, and more typically greater than about 20, typically involves crystallizing the zeolites from aqueous solution. For example, U.S. Pat. No. 3,702,886 to Argauer, et al., teaches a method of preparing ZSM-5 from a solution containing tetrapropyl ammonium hydroxide, sodium oxide, an oxide of aluminum or gallium, an oxide of silica or germanium, and water. The digestion of the gel particles is carried out until crystals form. The crystals are separated from the liquid and recovered.

A variation of the preparation procedure involves using clay as a source of alumina in preparing high silica zeolites. For example, U.S. Pat. No. 4,091,007 discloses a method for preparing a crystalline aluminosilicate zeolite, specifically ZSM-4 or ZSM-5, from a reaction mixture where at least about 70 weight percent of the alumina is provided by an alumina-containing clay added to the reaction mixture. EPO A2/0,156,595, discloses the preparation of crystalline zeolites having a silica to alumina mole ratio greater than 12 and a Constraint Index of 1 to 12 by forming a mixture of seed crystals, a source of silica, a source of alumina and water into shaped particles, which are then crystallized in an aqueous reaction mixture containing a source of alkali cations. It is also taught that alumina-containing clay may be used as an alumina source. U.S. Pat. No. 4,522,705 is directed to a catalytic cracking catalyst comprising an additive prepared by the in-situ crystallization of a clay aggregate disclosed in EPO A2/0,156,595. U.S. Pat. No. 5,145, 659 teaches methods for increasing the silica content of a zeolite supported on a matrix, where the matrix may be a clay.

Special methods for preparing the reaction mixture from which a zeolite may be crystallized have also been proposed. In U.S. Pat. No. 4,560,542 a dried hydrogel containing silica and alumina is contacted with a fluid medium containing an organic templating agent and maintained at specified crystallization conditions to form a crystalline aluminosilicate.

In U.S. Pat. No. 5,240,892 a reaction mixture containing at least about 30 weight percent solids content of alumina and precipitated silica is taught for preparing zeolites. The method of preparing the reaction mixture allows agitation of the mixture during crystallization, in spite of the high solids content of the mixture.

Zeolite crystallization from reaction mixtures initially containing a gel-like phase in equilibrium with an excess of liquid phase is disclosed in R. Aiello, et al., "Zeolite Crystallization from Dense Systems", *Materials Engineering* 1992, Vol. 3, n. 3, pp.407–416.

Other approaches to synthesis of crystalline zeolites have included preparing the zeolites in an essentially aqueous-free environment. These non-aqueous methods have been described, for example, in *ZEOLITES*, 1992, Vol 12, Apr./May, p. 343; *ZEOLITES* 1990, vol 10, Nov./Dec., p. 753; *ZEOLITES* 1989, vol 9, November, p. 468; Nature, Vol 317(12), September 1985, p. 157; and *J. Chem. Soc., Chem. Commun.*, 1988, p. 1486. *J. chem. Soc., Chem. Commun.*, 1993, p. 659 describes a kneading method for synthesizing ZSM-35 in a nonaqueous system, in which the amount of liquids used to prepare a crystallization mixture is not sufficient to wet all the solid particles so that the conglomerate reactant is actually a mixture of dry powder and small doughy lumps.

Though some of the methods described above reduce the number of steps in crystallizing zeolites, none of the cited patents provide a crystallization method which combines the ease of forming raw materials and a minimum of water into shaped particles, and crystallizing the zeolites within the shaped particles while eliminating an external liquid crystallization phase which must be treated or disposed of after the crystallization is complete.

SUMMARY OF THE INVENTION

Accordingly, it is an object of the present invention to provide a method for preparing crystalline zeolites in the form of shaped particles.

It is a further object of the invention to provide a method for preparing crystalline zeolites using a minimum of liquid for crystallization.

It is a further object of the invention to provide a method for preparing crystalline zeolites while minimizing an aqueous waste stream.

It is a further object of the invention to provide a method for preparing zeolites in the absence of added binder.

It is a further object of the invention to provide a method for preparing zeolites in commercially useful forms without any post crystallization forming steps.

It is a further object of the invention to provide a method for preparing zeolites having a small crystallite size.

It is a further object of the invention to provide a method for preparing zeolites using reduced amounts of a templating agent.

It is a further object of the invention to provide a method for preparing zeolites at reduced raw material costs.

These and further objects and advantages, which will be apparent to those skilled in the art, are realized in accordance with the present invention wherein a crystalline zeolite is prepared by a method comprising preparing a reaction mixture comprising at least one active source of silica, an organic templating agent capable of forming said crystalline zeolite, and sufficient water to shape said mixture; and heating said reaction mixture at crystallization conditions and in the absence of an external liquid phase for sufficient time to form a crystallized material containing crystals of said zeolite, wherein said zeolite crystals have a silica/alumina molar ratio greater than 12. The reaction mixture may optionally comprise at least one active source of alumina.

It is important, in preparing the reaction mixture of the present process, that the amount of water present in the reaction mixture as prepared for the crystallization step be sufficient to shape the mixture. While it is not a requirement to form the mixture into shaped particles before the mixture is subjected to crystallization conditions, it may be desired in many cases to do so. This amount of water is less than the amount of water required in conventional processes for preparing zeolites. Thus, during the crystallization step according to the present process, there is no separate liquid phase present which must be removed from the crystallized material at the end of the crystallization step by, for example filtering or decanting, prior to drying the crystals. Also, the amount of water present in the reaction mixture is insufficient to cause the shaped reaction mixture to collapse or "melt", i.e., once the reaction mixture is formed into the desired shape containing the desired amount of water, the resulting shape is self-supporting.

The present method is a general method for preparing zeolites having a silica/alumina molar ratio greater than 12. It is also a general method for preparing zeolites using organic templating agents. It is also a general method for preparing zeolites having a constraint index of greater than 1.

Among other factors, the present invention is based on the discovery of a method for crystallizing zeolites from a reaction mixture containing only enough water to form the mixture into a desired shape. Additional water beyond that needed to form the shaped particles is not necessary for crystallization. Furthermore, I have discovered that crystalline zeolites prepared according to the present process require lower levels of templating agent and reduced crystallization times relative to conventional zeolite crystallization methods. Further to my surprise, the zeolites prepared by the above described method are present in the shaped particles as very small crystallites.

DETAILED DESCRIPTION OF THE INVENTION PREPARING THE REACTION MIXTURE

The reaction mixture from which and in which the zeolite is crystallized comprises at least one active source of silica, an organic templating agent, and sufficient water to form the mixture into a desired shape. This amount of water is considerably less than that required in conventional processes for preparing zeolites.

The amount of liquid required in the reaction mixture of the present invention, where the liquid may include aqueous and, optionally, organic liquids, is that amount which is needed to adequately blend the mixture. Thus, a reaction mixture is prepared by mixing water with active sources of the zeolite to form a uniform mass having preferably a heavy paste-like consistency. The active sources will be in a form which can be easily blended into a uniform mass, and may be, for example, powders, hydrated particles, or concentrated aqueous solutions. Sufficient water is added to wet all the powders during the mixing and kneading steps. Alternatively, sufficient water is added that the powders may be kneaded into a uniform and generally homogeneous mixture which may be formed into shaped particles. It is not necessary that all of the active sources be readily soluble in water during kneading, since the water added to the active sources will be insufficient to make a fluid-like mixture. The amount of water added depends on the mixing apparatus and on the active sources employed. Those familiar with the art can readily determine without undue experimentation the amount of liquid required to properly mix active sources of the zeolite. For example, hydrated sources of the zeolite may require relatively less water, and dried sources may require relatively more. Though it is preferred that the mixture be blended and kneaded until the mixture has a uniform, homogeneous appearance, the length of time devoted to kneading the mixture is not critical in the present invention.

The water content of the reaction mixture after blending and kneading may be further adjusted, for example, by drying or the addition of water, to facilitate forming shaped particles.

The solids content of the reaction mixture will depend on the zeolite desired. The zeolite made by the present process has a silica to alumina mole ratio of greater than 12. Zeolites having a very high silica to alumina ratio are within the scope of the process, included zeolites having a silica to alumina mole ratio of greater than 100. Also included are zeolites which are essentially aluminum free. Especially when commercial silica sources are used, aluminum is almost always present to a greater or lesser degree. Thus, by "aluminum free" is meant that no aluminum is intentionally added to the reaction mixture, e.g., as an alumina or aluminate reagent, and that to the extent aluminum is present, it occurs only as a contaminant in the reagents. Other metallic components which may be added to the reaction mixture include, for example, titanium, chromium, germanium, gallium, iron, boron and alkali and alkaline earth metals.

Typical sources of silicon oxide ($SiO_2$) include silicates, silica hydrogel, silicic acid, colloidal silica, fumed silica, tetraalkyl orthosilicates silica hydroxides, precipitated silica and clays. Typical sources of aluminum oxide ($Al_2O_3$) when used in the reaction mixture include aluminates, alumina, and aluminum compounds such as $AlCl_3$, $Al_2(SO_4)_3$, aluminum hydroxide ($Al(OH)_3$), kaolin clays, and other zeolites. Titanium, chromium, germanium, gallium, iron, boron can be added in forms corresponding to their aluminum and silicon counterparts. Salts, particularly alkali metal halides such as sodium chloride, can be added to or formed in the reaction mixture. They are disclosed in the literature as aiding the crystallization of zeolites while preventing silica occlusion in the lattice.

An organic templating agent capable forming the zeolite may be included in the reaction mixture. Typically, the templating agent will be an organic compound which contains nitrogen or phosphorus. The sources of organic nitrogen-containing cations may be primary, secondary or tertiary amines or quaternary ammonium compounds, depending on the particular zeolite product to result from crystallization from the reaction mixture. Non-limiting examples of quaternary ammonium compounds include salts of tetramethylammonium, tetraethylammonium, tetrapropylammonium, tetrabutylammonium, diethylammonium, triethylammonium, dibenzylammonium, dibenzyldimethylammonium, dibenzyldiethylammonium, benzyltrimethylammonium and 2-(hydroxylalkyl) trialkylammonium, where alkyl is methyl, or ethyl or a combination thereof. Non-limiting examples of amines useful in the present process include the compounds of trimethylamine, triethylamine, tripropylamine, ethylenediamine, propanediamine, butanediamine, pentanediamine, propanediamine, butanediamine, pentanediamine, hexanediamine, methylamine, ethylamine, propylamine, butylamine, dimethylamine, diethylamine, dipropylamine, benzylamine, aniline, pyridine, piperidine and pyrrolidine. Amines useful herein are those having a $pK_a$, in the range of between about 7 and about 12. It is an important feature of the present invention that the amount of templating agent required for the crystallization step is reduced relative to conventional zeolitic crystallization procedures. Thus, the molar ratio of templating agent to silica in the reaction mixture will be in the range of from zero (0) to about 0.5, preferably from about 0.01 to about 0.5, more preferably from about 0.01 to about 0.3.

The reaction mixture may also comprise one or more active sources of alkali metal oxide. Sources of lithium, sodium and potassium, are preferred. Any alkali metal compound which is not detrimental to the crystallization process are suitable here. Non-limiting examples include oxides, hydroxides, nitrates, sulfates, halogenides, oxalates, citrates and acetates. In the reaction mixture, the alkali metal/silica molar ratio is preferably in the range from zero (0) to about 0.5 and more preferably in the range from about 0.05 to about 0.3. The alkali metal compound may also contribute $OH^-$. Generally, zeolite synthesis is facilitated by the presence of $OH^-$ in the reaction mixture at a molar ratio $OH^-/SiO_2$ of about 0.05 to about 0.4, and preferably from about 0.05 to about 0.3.

In the preferred method of the present zeolite synthesis, a reaction mixture is formed containing one or more sources of alkali metal oxide, organic nitrogen-containing cations, hydrogen ions, an oxide of silicon, water, and optionally, an oxide of aluminum. In general, the reaction mixture will have a Ph of at least 7, and preferably between about 8 and 14.

Forming the Shaped Particles

The advantage of the present invention is that the reaction mixture may be formed into a desired shape before the crystallization step, thereby reducing the number of process steps required to prepare catalytic materials containing the zeolite prepared in the mixture. Prior to forming the reaction mixture, it may be necessary to change the liquid content of the reaction mixture, either by drying or by adding more liquid, in order to provide a formable mass which retains its shape. In general, for most shaping methods, water will generally comprise from about 20 percent to about 60 percent by weight, and preferably from about 30 percent to about 50 percent by weight of the reaction mixture.

In the preforming step, the reaction mixture is formed into shaped particles. Methods for preparing the particles are well known in the art, and include, for example, extrusion, spray drying, granulation, agglomerization and the like. The particles are preferably of a size and shape desired for the ultimate catalyst, and may be in the form of, for example, extrudates, spheres, granules, agglomerates and prills. The particles will generally have a cross sectional diameter between about 1/64 inch and about 1/2 inch, and preferably between about 1/32 inch and about 1/4 inch, ie. the particles will be of a size to be retained on a 1/64 inch, and preferably on a 1/32 inch screen and will pass through a 1/2 inch, and preferably through a 1/4 inch screen.

In the present method, the shaped particles prepared from the reaction mixture will contain sufficient water to retain a desired shape. Additional water is not required in the mixture in order to initiate or maintain crystallization within the shaped particle. Indeed, it may be preferable to remove some of the excess water from the shaped particles prior to crystallization. Convention methods for drying wet solids can be used to dry the shaped particles, and may include, for example drying in air or an inert gas such as nitrogen or helium at temperatures below about 200° C. and at pressures from subatmospheric to about 5 atmospheres pressure.

Naturally occurring clays, e.g., bentonite, kaolin, montmorillonite, sepiolite and attapulgite, are not required, but may be included in the shaped particles prior to crystallization to provide particles having good crush strength. Such clays can be used in the raw state as originally mined or can be initially subjected to calcination, acid treatment or chemical modification. Microcrystalline cellulose has also been found to improve the physical properties of the particles.

Zeolite Crystallization

According to the present process, zeolites are crystallized either within the reaction mixture or within the shaped particles made from the reaction mixture. In either case, the composition of the mixture from which the zeolites are crystallized has the following molar composition ranges:

$SiO_2/Al_2O_3=5-28$ $M^{30}/SiO_2=0-1$ $R/SiO_2=0-0.5$ $OH^-/SiOhd\ 2=0.05-0.4$ $H_2O/SiO_2=0.5-5$ wherein $M^+$ is a alkali metal cation and R is a templating agent. More preferably, the molar composition ranges are as follows:

$SiO_2/Al_2O_3=12-28$ $M^{30}/SiO_2=0.03-0.5$ $R/SiO_2=0.01-0.3$ $OH^-/SiO_2=0.05-0.3$ $H_2O/SiO_2=1-4$ wherein $M^+$ is a alkali metal cation and R is a templating agent. Even more preferably, the $H_2O/Si_2$ molar composition will range from 1–3.

As stated above, the liquid present in the reaction mixture (which may be in the form of shaped particles) may be a combination of aqueous and organic liquids, so long as the specified amount of water is present. Since the total liquid content may affect, for example, the physical strength of the shaped particles, it is preferred that the total volatiles content of the reaction mixture during crystallization be in the range of between about 20% and about 60% (w/w), and preferably between about 30% and about 60% (w/w), where the total volatiles content is the measure of total volatile liquid, including water, in the reaction mixture. It is a feature of the present process that no additional liquid beyond that required to form the shaped particles is required for zeolite crystallization within the particles.

Crystallization of the zeolite takes place in the absence of an external liquid phase, i.e., in the absence of a liquid phase separate from the reaction mixture. In general, it is not detrimental to the present process if some liquid water is present in contact with the reaction mixture or with the shaped particles during crystallization, and it can be expected that some water may be on the surface of the shaped particles during crystallization. However, it is an objective of the present invention to provide a method of crystallizing zeolites in such a way as to minimize the amount of water which must be treated and/or discarded following crystallization. To that end, the present method provides a zeolite synthesis method which requires no additional water for crystallization beyond a sufficient amount of liquid required to form the particles. Indeed, under certain conditions, liquid water present during crystallization may alter the form of the shaped particles, and, in extreme circumstances, may cause the shaped particles to lose their integrity or to dissolve. Thus, the amount of liquid employed during crystallization is dictated largely by the requirements for forming shaped particles from active sources of the crystalline zeolite.

Crystallization is conducted at an elevated temperature and usually in an autoclave so that the reaction mixture is subject to autogenous pressure until the crystals of zeolite are formed. The temperatures during the hydrothermal crystallization step are typically maintained from about 80° C. to about 200° C., preferably from about 90° C. to about 180° C. and more preferably from about 100° C. to about 170° C.

It is an important feature of the present process that the crystallization of zeolites is frequently accelerated relative to conventional crystallization methods. Thus, the crystallization time required to form crystals will typically range from about 1 hour to about 10 days, and more frequently from about 3 hours to about 4 days. Under certain circumstances, crystallization times of less than 24 hours are required to prepare crystallized material of high crystallinity. In the present method, the crystallized material collected following the crystallization step will typically comprise at least about 50 weight percent crystals. Crystallized material containing at least about 80 weight percent crystals, and even at least about 90 weight percent crystals, may also be prepared using the present method.

Once the zeolite crystals have formed, the crystals may be water-washed and then dried, e.g., at 90° C. to 150° C. for from 8 to 24 hours. The drying step can be performed at atmospheric or subatmospheric pressures.

Seed Crystals

The zeolites of the present process are crystallized within the reaction mixture, which comprises amorphous, non-crystalline reagents. Crystalline material (ie. "seed" crystals) may be added to the mixture prior to the crystallization step, and methods for enhancing the crystallization of zeolites by adding "seed" crystals are well known. However, the addition of seed crystals is not a requirement of the present process. Indeed, it is an important feature of the present process that zeolites can be crystallized within the reaction mixture in the absence of crystals added prior to the crystallization step.

Description of Zeolites

In the most general embodiment, the present method is applicable to the synthesis of zeolites having a silica/ alumina molar ratio greater than 12. In a more specific embodiment, the method is useful for preparing silicate and aluminosilicate zeolites having a Constraint Index of greater than about 1. The Constraint Index as used herein is defined in J. Catalysis 67, page 218 and also disclosed in U.S. Pat. No. 4,481,177.

Specific, non-limiting examples of crystalline zeolites which may be prepared by the present method include ZSM-5, ZSM-11, ZSM-12, ZSM-22, ZSM-23, SSZ-35, ZSM-38, beta, SSZ32, silicalite and other similar materials.

According to the present process, a reaction mixture is prepared having a composition, in terms of mole ratios, falling within the following ranges:

|  | Broad | Preferred |
|---|---|---|
| $YO_2/W_2O_3$ | 12–∞ | 12–∞ |
| $M^+/YO_2$ | 0–1 | 0.04–0.7 |
| $R/YO_2$ | 0–0.5 | 0.01–0.3 |
| $OH^-/YO_2$ | 0.05–0.4 | 0.05–0.3 |
| $H_2O/YO_2$ | 0.5–5 | 1–4 |

Y is silicon, germanium or both, W is aluminum, boron, gallium, iron, or a mixture thereof, $M^+$ is an alkali metal ion, preferably sodium and R is a templating agent. The type of zeolite crystallized from the reaction mixture depends on a number of factors, including crystallization conditions, specific composition of the reaction mixture and the type of templating agent used.

Zeolite ZSM-5 and the conventional preparation thereof are described in U.S. Pat. No. 3,702,886, the disclosure of which is incorporated herein by reference. The reaction mixture from which ZSM-5 can be suitably prepared is formed by mixing sources of silica and alumina with a templating agent, preferably tetrapropylammonium hydroxide, and sources of an alkali metal oxide, preferably sodium oxide.

Zeolite SSZ-35, and the conventional preparation thereof, are disclosed in pending patent application U.S. Ser. No. 959,205, the disclosure of which is incorporated herein by reference. The aqueous reaction mixture prepared in the process for making SSZ-35 zeolites contains sources of an alkali metal oxide, a relatively rigid polycyclic ring system templating agent having a quaternary nitrogen heteroatom (eg. N,N-dimethyl-4-azoniatricyclo[5.2.2.0$^{(2,6)}$]undec-8-ene cation), an oxide of aluminum, boron, gallium, iron or mixtures thereof, and an oxide of silicon or germanium, or mixture of the two.

Zeolite beta and the conventional preparation thereof are described in U.S. Pat. No. 3,308,069, the disclosure of which is incorporated herein by reference. The reaction mixture from which zeolite beta can be suitably prepared is formed by mixing sources of silica and alumina with a templating agent, preferably tetraethylammonium hydroxide (TEAOH), and sources of an alkali metal oxide, preferably sodium oxide. The crystallization procedures can be satisfactorily carried out at temperatures within the range from about 75° C. to about 200° C. Heating under autogenous pressure is carried out until desired crystalline zeolite product is formed.

Zeolite boron beta and the conventional preparation thereof are described in U.S. Pat. Nos. 4,788,169 and 5,166,111, the disclosures of which are incorporated herein by reference. Boron beta zeolites can be suitably prepared from a reaction mixture containing sources of an alkali metal borate, a templating agent such as tetraethylammonium hydroxide or bis(1-azonia, bicyclo[2.2.2]octane)-α, ω alkane diquaternary ammonium ion, and an oxide of silicon or germanium, or mixture of the two. The reaction mixture should have a composition in terms of mole ratios falling within the following ranges:

|  | Broad | Preferred |
|---|---|---|
| $YO_2/W_2O_3$ | 10–200 | 30–100 |
| $OH/YO_2$ | 0.10–1.0 | 0.25–0.50 |
| $Q/YO_2$ | 0.05–0.50 | 0.25–0.35 |
| $M^+/YO_2$ | 0.05–0.30 | 0.05–0.10 |
| $H_2O/YO_2$ | 0.5–5 | 1–4 |
| $Q/Q + M^+$ | 0.30–0.90 | 0.60–0.80 | wherein Q is the templating agent, Y is silicon, germanium or both, and W is boron. M is an alkali metal, preferably sodium. The organic compound which acts as a source of the quaternary ammonium ion employed can provide hydroxide ion.

The reaction mixture is prepared using standard zeolitic preparation techniques. Sources of boron for the reaction mixture include borosilicate glasses and most particularly, other reactive borates such as sodium borate and borate esters. Typical sources of silicon oxide include precipitated silica, silicates, silica hydrogel, silicic acid, colloidal silica, tera-alkyl ortho-silicates, and silica hydroxides.

The reaction mixture in the preparation of boron beta is maintained at an elevated temperature until the crystals of the zeolite are formed. The temperatures during the hydrothermal crystallization step are typically maintained from about 140° C. to about 200° C., preferably from about 150°C. to about 170° C. and most preferably from about 135° C. to about 165° C. The crystallization period is typically greater than one day and preferably from about three days to about seven days.

The hydrothermal crystallization is conducted under pressure and usually in an autoclave so that the reaction mixture is subject to autogenous pressure.

Zeolite ZSM-12 and the conventional preparation thereof are described in U.S. Pat. No. 3,832,449, the disclosure of which is incorporated herein by reference. Zeolite ZSM-12 can be suitably prepared by preparing a reaction mixture containing tetraethyl ammonium cations, sodium oxide, an oxide of aluminum or gallium, an oxide of silica or germanium, and water. Thereafter, the crystals are separated from the liquid and recovered. Typical reaction conditions consist of heating the foregoing reaction mixture to a temperature of from about 80° C. to 180° C. for a period of time of from about 1 hour to 10 days. A more preferred temperature range is from about 150° C. to 170° C. with the amount of time at a temperature in such a range being from about 3 hours to 4 days.

ZSM-22 and the conventional preparation thereof are described in U.S. Pat. No. 4,556,477, the disclosure of which is incorporated herein by reference. Zeolite ZSM-22 can be suitably prepared by preparing a reaction mixture containing an alkali metal oxide, a source of silica, an organic compound of an element of Group IVB, including nitrogen or phosphorous which contains at least one alkyl or aryl group having at least 2 carbon atoms. The reaction mixture is maintained at crystallization conditions until crystals of the zeolite are formed. Thereafter, the crystals are separated from the liquid and recovered. Typical reaction conditions consist of heating the foregoing reaction mixture to a temperature of from about 80° C. to 200° C. for a period of time of from about 1 hour to 10 days.

Silicalite and the conventional preparation thereof are described in U.S. Pat. No. 4,073,865, the disclosure of which is incorporated herein by reference. Furthermore, the reaction mixture used in the preparation of silicalite has no added active sources of alumina. Thus, the sources of alumina in the reaction mixture are present at very low, ie. impurity, levels. The templating agent useful for the crystallization of silicalite is preferably a quaternary cation having the formula $(R_4X)^+$, in which each R represents hydrogen or an alkyl group containing from 2 to 6 carbon atoms, and X represents phosphorus or nitrogen. The reaction mixture thus provides is heated at a temperature of from 100° C. to 200° C. until a crystalline hydrated precursor is formed, usually about 1 hour to 10 days, isolating said crystalline precursor and calcining same at a temperature of from 400° C. to 1000° C.

Zeolite ZSM-11 and the conventional preparation thereof are described in U.S. Pat. No. 3,709,979, the disclosure of which is incorporated herein by reference. Zeolite ZSM-35 and the conventional preparation thereof are described in U.S. Pat. No. 4,016,245, the disclosure of which is incorporated herein by reference. ZSM-38 and the conventional preparation thereof are described in U.S. Pat. No. 4,046,859, the disclosure of which is incorporated herein by reference.

Zeolite ZSM-23 and the conventional preparation thereof are described in U.S. Pat. Nos. 4,076,842, 4,296,083 and 4,490,342, the disclosure of which, and particular the methods of preparation and the templating agents used in the preparation, are incorporated herein by reference. Zeolite SSZ-32 and the conventional preparation thereof are described in U.S. Pat. No. 5,053,373, the disclosure of which is also incorporated herein by reference. ZSM-23 type zeolites can be suitably prepared from a reaction mixture containing sources of an alkali metal oxide, a templating agent, an oxide of aluminum, and preferably wherein the aluminum oxide source provides aluminum oxide which is in a covalently dispersed form on silica, and an oxide of silicon. The reaction mixture should have a composition in terms of mole ratios falling within the following ranges:

|  | Broad | Preferred |
| --- | --- | --- |
| $SiO_2/Al_2O_3$ | 20–5000 | 30–2000 |
| $OH^-/SiO_2$ | 0.10–1.0 | 0.20–0.40 |
| $Q/SiO_2$ | 0.01–2.0 | 0.05–1.0 |
| $M^+/SiO_2$ | 0.01–2.0 | 0.10–1.0 |
| $H_2O/SiO_2$ | 0.5–5 | 1–4 |
| $Q/Q + M^+$ | 0.25–0.95 | 0.33–0.67 | wherein Q is the templating agent, M is an alkali metal ion, preferably sodium or potassium. The organic cation compound which acts as a source of the quaternary ammonium ion employed can provide hydroxide ion.

Preferred templating agents suitable for preparing ZSM-23 type zeolites include pyrrolidine, Diquat-7, of the formula $(CH_3)_3N^{30}$——$R_1$——$N^+(CH_3)_3$, wherein $R_1$ is a saturated or unsaturated straight chain hydrocarbon group having seven carbon atoms, and N-lower alkyl-N'-isopropyl-imidazolium cation such as N,N'diisopropyl-imidazolium cation or N-methyl-N'-isopropyl-imidazolium cation. Representative anions associated with the organic cation templating agents include halogens, e.g., fluoride, chloride, bromide and iodide, hydroxide, acetate, sulfate, carboxylate, etc. Hydroxide is the most preferred anion.

Typical sources of aluminum oxide for the reaction mixture include aluminates, alumina, and aluminum compounds, such as aluminum-coated colloids, $Al_2(SO_4)_3$, and other zeolites.

Typical sources of silicon oxide include precipitated silica, silicates, silica hydrogel, silicic acid, colloidal silica, fumed silicas, tetraalkyl orthosilicates, and silicic hydroxides. Salts, particularly alkali metal halides such as sodium chloride, can be added to or formed in the reaction mixture. They are disclosed in the literature as aiding the crystallization of zeolites while preventing silica occlusion in the lattice.

The reaction mixture in the preparation of ZSM-23 and SSZ-32 type zeolites is maintained at an elevated temperature until the crystals of the zeolite are formed. The temperatures during the hydrothermal crystallization step are typically maintained from about 140° C. to about 200° C., preferably from about 160° C. to about 180° C. and most preferably from about 170° C. to about 180° C. The crystallization period is typically greater than 1 day and preferably from about 5 days to about 10 days.

The hydrothermal crystallization is conducted under pressure and usually in an autoclave so that the reaction mixture is subject to autogenous pressure.

Zeolite Crystallite Size

An important feature of the present process is the small crystallite size of zeolite crystals formed in the process. Typically, the zeolite crystals are less than 10 micron in diameter as determined by Scanning Electron Microscopy. Since small crystals are desirable for certain catalytic applications, crystallization conditions can be tailored to product zeolite crystals with diameters of less than 1.0 microns. The crystal size of the zeolite may be determined by, for example, grinding the shaped particles to separate the individual crystals. High resolution electron micrographs of the separated crystals can then be prepared, after which the average size of individual zeolite crystals can be determined by reference to calibrated length standards. An average crystal size may then be computed in various well-known ways, including:

$$\text{Number Average} = \frac{\sum\limits_{i=1}^{n} (n_i \times L_i)}{\sum\limits_{i=1}^{n} n_i}$$

where $n_i$ is the number of zeolite crystals where minimum length falls within an interval $L_i$. For purposes of this disclosure, average crystal size will be defined as a number average. It is important to note that for purposes of this invention, zeolite crystal size is distinguished from what some manufacturers term "zeolite particle size" the latter being the average size of all particles, including both individual crystals and polycrystalline agglomerates, in the as-produced zeolite powder.

Typically, the zeolite crystals are less than 10 micron in diameter as determined by Scanning Electron Microscopy. Since small crystals are desirable for certain catalytic applications, crystallization conditions can be tailored by, for example, reducing crystallization temperature, by increasing aluminum content in the reaction mixture, and/or by reducing the water content of the reaction mixture or the shaped particles prior to crystallization, to produce zeolite crystals with diameters of less than 1.0 micron.

Zeolite Post-Treatment

A crystallized material containing crystals of zeolite are prepared in the process as described above. The synthetic zeolite can be used as synthesized or can be thermally treated (calcined). Usually, it is desirable to remove the alkali metal cation by ion exchange and replace it with hydrogen, ammonium, or any desired metal ion. The zeolite can be leached with chelating agents, e.g., EDTA or dilute acid solutions, to increase the silica:alumina mole ration. These methods may also include the use of $(NH_4)_2SiF_6$ or acidic ion-exchange resin treatment. The zeolite can also be steamed; steaming helps stabilize the crystalline lattice to attack from acids. The zeolite can be used in intimate combination with hydrogenating components, such as tungsten, vanadium, molybdenum, rhenium, nickel, cobalt, chromium, manganese, or a noble metal, such as palladium or platinum, for those applications in which a hydrogenation-dehydrogenation function is desired. Typical replacing cations can include metal cations, e.g., rare earth, Group IA, Group IIA and Group VIII metals, as well as their mixtures. Of the replacing metallic cations, cations of metals such as rare earth, Mn, Ca, Mg, Zn, Ga, Cd, Pt, Pd, Ni, Co, Ti, Al, Sn, Fe and Co are particularly preferred.

The hydrogen, ammonium, and metal components can be exchanged into the zeolite. The zeolite can also be impregnated with the metals, or, the metals can be physically intimately admixed with the zeolite using standard methods known to the art. And, the metals can be occluded in the crystal lattice by having the desired metals present as ions in the reaction mixture from which the zeolite is prepared.

Typical ion exchange techniques involve contacting the synthetic zeolite with a solution containing a salt of the desired replacing cation or cations. Although a wide variety of salts can be employed, chlorides and other halides, nitrates, and sulfates are particularly preferred. Representative ion exchange techniques are disclosed in a wide variety of patents including U.S. Pat. Nos. 3,140,249; 3,140,251; and 3,140,253. Ion exchange can take place either before or after the zeolite is calcined.

Following contact with the salt solution of the desired replacing cation, the zeolite is typically washed with water and dried at temperatures ranging from 65C. to about 315C. After washing, the zeolite can be calcined in air or inert gas at temperatures ranging from about 200C. to 820C. for periods of time ranging from 1 to 48 hours, or more, to produce a catalytically active product especially useful in hydrocarbon conversion processes.

Regardless of the cations present in the synthesized form of the zeolite, the spatial arrangement of the atoms which form the basic crystal lattice of the zeolite remains essentially unchanged. The exchange of cations has little, if any, effect on the zeolite lattice structures.

The zeolites may be used as catalysts, without additional forming, when the shaped particles, formed from the reaction mixture described hereinbefore, are of a size and shape desired for the ultimate catalyst. Alternatively, the zeolite can be composited with other materials resistant to the temperatures and other conditions employed in organic conversion processes, using techniques such as spray drying, extrusion, and the like. Such matrix materials include active and inactive materials and synthetic or naturally occurring zeolites as well as inorganic materials such as clays, silica and metal oxides. The latter may occur naturally or may be in the form of gelatinous precipitates, sols, or gels, including mixtures of silica and metal oxides. Use of an active material in conjunction with the synthetic zeolite, i.e., combined with it, tends to improve the conversion and selectivity of the catalyst in certain organic conversion processes. Inactive materials can suitably serve as diluents to control the amount of conversion in a given process so that products can be obtained economically without using other means for controlling the rate of reaction. Frequently, zeolite materials have been incorporated into naturally occurring clays, e.g., bentonite and kaolin. These materials, i.e., clays, oxides, etc., function, in part, as binders for the catalyst. It is desirable to provide a catalyst having good crush strength, because in petroleum refining the catalyst is often subjected to rough handling. This tends to break the catalyst down into powders which cause problems in processing.

Naturally occurring clays which can be composited with the synthetic zeolites of this invention include the montmorillonite and kaolin families, which families include the sub-bentonites and kaolins commonly known as Dixie, McNamee, Georgia and Florida clays or others in which the main mineral constituent is halloysite, kaolinite, dickite, nacrite, or anauxite. Fibrous clays such as sepiolite and attapulgite can also be used as supports. Such clays can be used in the raw state as originally mined or can be initially subjected to calcination, acid treatment or chemical modification.

In addition to the foregoing materials, the zeolite prepared by the present method can be composited with porous matrix materials and mixtures of matrix materials such as silica, alumina, titania, magnesia, silica-alumina, silica-magnesia, silica-zirconia, silica-thoria, silica-beryllia, silica-titania, titania-zirconia as well as ternary compositions such as silica-alumina-thoria, silica-alumina-zirconia, silica-alumina-magnesia and silica-magnesia-zirconia. The matrix can be in the form of a cogel.

The zeolite can also be composited with other zeolites such as synthetic and natural faujasites (e.g., X and Y), erionites, and mordenites. They can also be composited with purely synthetic zeolites such as those of the ZSM, EU, FU, and NU series. The combination of zeolites can also be composited in a porous inorganic matrix.

Zeolites prepared in the present process are useful in hydrocarbon conversion reactions. Hydrocarbon conversion reactions are chemical and catalytic processes in which carbon containing compounds are changed to different carbon containing compounds. Examples of hydrocarbon conversion reactions include catalytic dewaxing, catalytic cracking, hydrocracking, and olefin and aromatics formation reactions, including formation from oxygenates. The catalysts are useful in other petroleum refining and hydrocarbon conversion reactions such as isomerizing n-paraffins and naphthenes, polymerizing and oligomerizing olefinic or acetylinic compounds such as isobutylene and pentene-1, reforming, alkylating, isomerizing polyalkyl substituted aromatics (e.g. meta xylene), and disproportionating aromatics (e.g. toluene) to provide mixture of benzene, xylenes and higher methylbenzenes.

EXAMPLES

Example 1

To 100 grams of silica (Hi-Sil 233, a hydrated silica manufactured by PPG) were added 8 grams of kaolin clay powder (53.7 wt % $SiO_2$, 42.5 wt % $Al_2O_3$) and 60 grams of a 40 wt % aqueous solution of tetrapropylammonium hydroxide (TPAOH) and mixed for one hour in a Baker-Perkins mixer. Then 0.34 grams of boric acid (H3BO3) were dissolved in 25 grams of water and added to the above mixture along with 5.8 grams of a 50 wt % aqueous solution of NaOH. Mixing continued for another 30 minutes. The molar ratios in the synthesis mix were as follows:

$TPA^+/SiO_2=0.074$ $OH^-/SiO_2=0.12$ $Na^+/SiO_2=0.045$ $SiO_2/Al_2O_3=48$ $H_2O/SiO_2=2.6$

The mixture was then extruded through a 1/16-inch die. The extrudate was placed in a sealed Teflon bottle and heated at autogenous pressure at 100° C. for four days. The extrudate was then dried overnight at 110° C. in a vacuum oven and calcined in air at 538° C. for eight hours. The product was identified as about 100% ZSM-5 by X-ray diffraction analysis, and was composed of particles about 0.2 microns in diameter as determined by scanning electron microscopy (SEM). Sodium was 1.5 wt %. The crush strength of the extrudate was 2.1 lb/mm.

Example 2

To 50 grams of Hi-Sil 233 were added 4 grams of kaolin clay powder and mixed for five minutes in a Baker-Perkins mixer. Four grams of a 50 wt % aqueous solution of NaOH were added and mixed another ten minutes. To this mixture were added 45 grams of a 40 wt % aqueous solution of TPAOH and mixing continued another 15 minutes. The mixture was extruded through a 1/16-inch die and air dried for one hour before being placed in a sealed Teflon bottle in a stainless steel pressure vessel and heated at 100° C. for four days at autogenous pressure. The extrudate was then dried overnight in a vacuum oven at 110° C. and calcined in air at 538° C. for eight hours. The product was identified as about 100% ZSM-5 by X-ray diffraction analysis. The average particle size as determined by SEM was about 0.1 microns.

Example 3

To 50 grams of Hi-Sil 233 were added 2 grams of 50% NaOH and mixed for five minutes in a Baker-Perkins mixer. To this were added 3 grams of microcrystalline cellulose (Avicel, manufactured by FMC Corporation) along with 30 grams of a 40 wt % aqueous solution of TPAOH and mixed for 15 minutes. Then 0.17 grams of H3BO3 were dissolved in 15 grams of water and this solution added to the above mix with mixing for an additional 10 minutes. Molar ratios in the synthesis mix were as follows:

$TPA^+/SiO_2=0.074$ $OH^-/SiO2=0.11$ $Na^+/SiO_2=0.033$ $H_2O/SiO_2=2.5$

The mixture was extruded through a 1/16-inch die. The extrudate was equally divided with each half placed in a Teflon bottle in a stainless steel pressure vessel and heated for four days at autogenous pressure. The first sample was run at 100° C. and the second at 120° C. The products was dried overnight at 110° C. in a vacuum oven and calcined in air for eight hours at 538° C. Both products were found by X-ray diffraction analysis to be about 100% silicalite. SEM showed the zeolite made at 100° C. to have an average particle size of about 0.2 microns while that made at 120° C. had an average particle size of about 0.4 microns.

The crush strength of the first extrudate was 1.3 lb/mm while that of the second was 0.9 lb/mm.

Example 4

To 50 grams of Hi-Sil 233 were added 4 grams of sepiolite clay powder (Tolsa) and mixed for 5 minutes in a Baker-Perkins mixer. Then 30 grams of a 40 wt % aqueous solution of TPAOH were added with mixing for 15 minutes. Next 0.17 grams of H3BO3 were dissolved in 9 grams of water and this solution along with 4 grams of a 50wt % aqueous solution of NaOH were added to the above mixture and mixed an additional 10 minutes. The mixture was extruded through a 1/16-inch die. Molar composition of the extrudate was as follows:

$TPA^+/SiO_2=0.074$ $OH^-/SiO_2=0.13$ $Na^+/SiO_2=0.066$ $SiO_2/Al_2O_3=310$ $H_2O/SiO_2=2.3$

The extrudate was placed in a Teflon bottle in a stainless steel pressure vessel and heated for four days at 100° C. and autogenous pressure. The extrudate was then dried overnight at 110° C. in a vacuum oven and calcined in air at 538° C. for eight hours. X-ray diffraction analysis showed the product to be about 100% ZSM-5. The average particle size from SEM was below 0.1 microns. The crush strength of the extrudate was 4.4 lb/mm.

Example 5

To 800 grams of Hi-Sil 233 were added 64 grams of a 50 wt % aqueous solution of NaOH and 64 grams of kaolin clay powder and mixed for 30 minutes in a Baker-Perkins mixer. To this was added a solution of 2.4 grams of H3BO3 dissolved in 200 grams of water along with 480 grams of a 40 wt % aqueous solution of TPAOH with mixing for about 90 minutes. Three hundred grams of water were then added gradually over the next three hours with mixing. Mixing continued for another half hour with the mixer walls heated to 100° C. to reduce the volatiles content of the mix (measured on a small sample at about 427° C.) to 52.5%. The mix was then extruded through a multiple-holed 1/16-inch die. About one-third of the extrudate was allowed to air dry at room temperature to 44.7% volatiles. Molar composition of the extrudate was as follows:

$TPA^+/SiO_2=0.074$ $OH^-/SiO_2=0.12$ $Na^+/SiO_2=0.063$ $SiO_2/Al_2O_3=48$ $H_2O/SiO_2=2.2$

Both portions were placed in Teflon bottles in stainless steel pressure vessels and heated at 100° C. and autogenous pressure for four days. The extrudates were dried at 110° C. in a vacuum oven overnight and calcined in air for eight hours at 538° C. X-ray diffraction analysis showed both samples to be about 100% ZSM-5. The average particle size by SEM of the sample which was not air dried before crystallization was about 0.2 microns and the extrudate crush strength 1.0 lb/mm. The average particle size of the sample which was air dried was less than 0.1 microns and the extrudate crush strength was 3.1 lb/mm.

Example 6

In this example, zeolite was crystallized in-extrudate without the use of a high pressure autoclave. 50 grams of Hi-Sil 233 were mixed with 4 grams of kaolin clay powder in a Baker-Perkins mixer for 5 minutes. Then 30 grams of a 40 wt % aqueous solution of TPAOH were added and mixed for 15 minutes. A solution of 0.17 grams H3BO3 dissolved in 15 grams of water was added along with 4 grams of a 50 wt % aqueous solution of NaOH and mixing continued for 10 minutes. The mix was extruded and the extrudate then placed on a screen through which steam was passed from the bottom. After four days, the extrudate was dried overnight at 110° C. in a vacuum oven and calcined in air for eight hours at 538° C. The product was identified as ZSM-5 by X-ray diffraction analysis. The average particle size by SEM was about 0.3 microns.

Example 7

An extrudate made similar to that of Example 1 was impregnated with 0.8 wt % Pt by the pore-fill method using an aqueous solution of $Pt(NH_3)_4(NO_3)_2$. The catalyst was then dried overnight in a vacuum oven at 110° C. and calcined in dry air for 4 hours at 204° C., 4 hours at 260° C., and 4 hours at 288° C. The catalyst was used to reform a 100.6 research octane number (RON) reformate (Table I) at 70 psig, 1.3 LHSV, and a hydrogen to fresh feed hydrocarbon (H2/HC) ratio of 1. The catalyst was tested both unsulfided and sulfided. Unsulfided, a 107 RON was obtained at a catalyst temperature of 770 F with a C5+ yield of 85.7 wt %. After sulfiding, the required catalyst temperature for 107 RON rose to 915° F., but the C5+ increased to 93 wt %.

Example 8

To 50 grams of Hi-Sil 233 were added 4 grams of kaolin clay powder and mixed in a Baker-Perkins mixer for 5 minutes. Then 6 grams of $NaAlO_2$ were dissolved in 30 grams of a 40 wt % aqueous solution of tetraethylammonium hydroxide (TEAOH) with heating and added to the above along with one gram of a 50 wt % aqueous solution of NaOH and mixed for about 15 minutes. 15 more grams of 40% TEAOH were added, followed by 3.2 grams of $NaNO_3$ and 5 grams of water with mixing for an additional 30 minutes. Molar ratios in the synthesis mix were as follows:

$TEA^+/SiO_2=0.15$ $OH^-/SiO_2=0.18$ $Na^+/SiO_2=0.17$ $SiO_2/Al_2O_3=15$ $H_2O/SiO_2=2.7$

The mix was extruded through a 1/16-inch die and placed in a Teflon bottle in a stainless steel pressure vessel. and heated at 150° C. for four days at autogenous pressure. The extrudates were washed with water, dried overnight in a vacuum oven at 110° C. then calcined in air at 538° C. for eight hours. X-ray diffraction analysis showed the extrudate to contain beta zeolite with no other crystalline phases. By comparing the peak area from 20 to 24 degrees 2 theta to that of a commercial reference sample, the degree of crystallinity was determined to be about 92%. The average particle size by SEM was about 0.4 microns. The crush strength of the extrudate was 1.6 lb/mm. Example 9

To 100 grams of Hi-Sil 233 were added 8 grams of kaolin clay powder and mixed in a Baker-Perkins mixer for 5 minutes. 12 grams of $NaAlO_2$ were dissolved with heating in 120 grams of a 40 wt % aqueous solution of TEAOH and added to the above with 2 grams of a 50 wt % aqueous solution of NaOH. After 30 minutes of mixing, another 30 grams of 40% TEAOH were added in which was dissolved 6.4 grams of NaNO3. Mixing continued for another 30 minutes, then the mix was extruded through a 1/16-inch die and placed in a Teflon bottle in a stainless steel pressure vessel and heated at 100° C. and autogenous pressure for four days. The extrudate was washed with water adjusted to pH 10 with $NH_4OH$, dried overnight in a vacuum oven at 110° C., then calcined in air at 538° C. for eight hours. X-ray diffraction analysis showed the extrudate to contain beta zeolite with no other crystalline phases and a degree of crystallinity of about 82%. The average particle size by SEM was about 0.1 microns.

Example 10

To 100 grams Hi-Sil 233 were added 3 grams of $NaAlO_2$ and 12 grams of kaolin clay and mixed for 5 minutes. To this was added 90 grams of a 40 wt % aqueous solution of TEAOH and 2 grams of a 50 wt % aqueous solution of NaOH and mixed for about 15 minutes. Another 30 grams of 40% TEAOH were added along with 6.4 grams of $NaNO_3$ and mixed another 30 minutes. The mix was extruded, allowed to dry in air at room temperature for two hours, then re-extruded and allowed to dry for one hour. Molar ratios in the extrudate were as follows:

$TEA^+/SiO_2=0.20$ $OH^-/SiO_2=0.21$ $Na^+/SiO_2=0.08$ $SiO_2/Al_2O_3=24$

The extrudate was then placed in a Teflon bottle in a stainless steel pressure vessel and heated to 150° C. at autogenous pressure for four days. The extrudate was washed with water, dried overnight in a vacuum oven at 110° C., and calcined in air at 538° C. for eight hours. X-ray diffraction analysis showed the extrudate to be close to 100% beta.

Example 11

A beta extrudate was made similar to that of Example 8. This was exchanged for two hours at 82° C. with a four-fold excess of a 15 wt % aqueous solution of $CsNO_3$. The extrudate was then filtered and washed with water. It was then exchanged with a solution of $Pt(NH_3)_4(NO_3)_2$ to bring the Pt content of the extrudate to 0.6 wt %. The extrudate was then dried overnight in a vacuum oven at 110° C., and calcined in air at 149° C. for two hours, 204° C. for two hours, and 288° C. for four hours. The catalyst was used to reforming n-hexane at 482° C., 1.0 LHSV, 30 psig, and 2 HC/H2. At 10 hours onstream, conversion to benzene was 24 wt %, and selectivity to aromatics as a percent of C6 paraffin conversion was 54%.

Example 12

To 600 grams of Hi-Sil 233 were added 26 grams of $NaAlO_2$ and mixed in a Baker-Perkins mixer for 5 minutes. To this were then added 412 grams of a 35 wt % aqueous solution of TEAOH, followed by 100 grams of water and 48 grams of a 50 wt % aqueous solution of NaOH. After 3.5 hours of mixing, 240 grams of water were slowly added over a 25 minute period with mixing until the mix was uniformly wet. Then 36 grams of kaolin clay powder were added and slow mixing continued with the mixer walls heated to about 60° C. until a small sample of the mix could be extruded through a single-holed 32-inch die in a Carver press at 2500–3000 psi. The mix was then extruded through a multiple-holed 1/16-inch die and placed on screens to dry at room temperature to 45% volatiles. Molar ratios in the extrudate were as follows:

$TEA^+/SiO_2=0.11$ $OH^-/SiO_2=0.17$ $Na^+/SiO_2=0.10$ $SiO_2/Al_2O_3=24$ $H_2O/SiO_2=2.3$

The extrudate was then placed in a Teflon bottle in a stainless steel pressure vessel and heated to 150° C. at autogenous pressure for 3.5 days. The extrudate was then washed with water, dried over night in a vacuum oven at 120° C., and calcined in air at 593° C. for seven hours. X-ray diffraction analysis showed the extrudate to be about 90% beta zeolite.

Example 13

To 600 grams of Hi-Sil 233 in a Baker-Perkins mixer were added 18 grams of NaAlO$_2$ and 38.4 grams of NaNO$_3$ and mixed for one hour. To this were added 72 grams of kaolin clay powder, followed by 600 grams of a 40 wt % aqueous solution of TEAOH and 12 grams of a 50 wt % aqueous solution of NaOH. Mixing continued for 4 hours, after which time 110 grams of water were slowly added with mixing to form a thick paste. The mixer walls were then heated to about 70° C. and slow mixing continued until an extrudate could be produced from a small sample through a 1/32-inch die in a Carver press at 1500 psi. The volatiles level at this point was 52%. The mix was then extruded through a multiple-holed 1/16 inch die and placed on screens to dry to 45% volatiles at room temperature. Molar ratios in the extrudate were as follows:

$TEA^+/SiO_2=0.18$ $OH^-/SiO_2=0.20$ $Na^+/SiO_2=0.09$ $SiO_2/Al_2O_3=23$ $H_2O/SiO_2=2.1$

About one-fourth of the extrudate was placed in a Teflon bottle in a stainless steel pressure vessel and heated at 150° C. for four days at autogenous pressure. Another sample of the extrudate was heated in the same manner but for six days at 100° C. The extrudate was heated in the same manner but for six days at 100° C. The extrudate samples were washed with water, dried overnight in a vacuum oven, and calcined in air at 593° C. for 8 hours. X-ray diffraction analysis identified both samples as about 100% beta. The average crystal size by SEM in both samples was less than 0.2 microns. Both extrudates had crush strengths exceeding 2 lb/mm. Example 14

To 100 grams of Hi-Sil 233 were added 1.0 grams of NaAlO$_2$ and 6.0 grams of sepiolite clay powder. Then 90 grams of a 40 wt % aqueous solution of TEAOH and 2 grams of a 50 wt % aqueous solution of NaOH were added with mixing. After 15 minutes of mixing, 11.4 grams of NaNO$_3$, dissolved in 15 grams of water, were added with mixing for an additional 2.5 hours. To one-third of this mix was added 5 grams of water with mixing for about 15 minutes. The mix was then extruded through a 1/16-inch die. Molar ratios in the mix were as follows:

$TEA^+/SiO_2=0.16$ $OH^-/SiO_2=0.18$ $Na^+/SiO_2=0.11$ $SiO_2/Al_2O_3=160$ $H_2O/SiO_2=2.9$

The extrudate was placed in a Teflon bottle in a stainless steel pressure vessel and heated to 150° C. at autogenous pressure for three days. The extrudate was washed with water adjusted to pH 10 with NH$_4$OH, dried overnight in a vacuum oven at 120° C., and calcined in air at 593° C. for eight hours. X-ray diffraction analysis showed the extrudate to consist primarily of ZSM-12.

Example 15

150 grams of Hi-Sil 233 were placed in a Baker-Perkins mixer. To this was added 6.5 grams of NANO$_3$, 3.0 grams of kaolin clay powder, and 2.2 grams of alumina powder (Reheis F, 52.3 wt % Al$_2$O$_3$, 47.7 wt % water), and mixed for 5 minutes. Tothis was added 130 grams of a 1.4M solution of 1,3,3,8,8-pentamethyl-3-azoniabicyclo[3.2.1]octane hydroxide, followed by 12 grams of a 50 wt % aqueous solution of NaOH, and mixed for three hours. An additional 30 grams of the organic template solution were added followed by the slow addition of water over 25 minutes until uniformly wet clumps were formed. The mixer walls were heated to about 60° C. and slow mixing continued until the volatiles content of the mix was reduced to about 62%. The mix was extruded through a 1/16-inch die and the extrudate air dried to a volatiles content of 50%. Molar ratios were as follows:

$R/SiO_2=0.098$ $OH^-/SiO_2=0.16$ $Na^+/SiO_2=0.10$ $SiO_2/Al_2O_3=100$ $H_2O/SiO_2=3.7$

The extrudate was placed in a Teflon bottle in a stainless steel pressure vessel and heated for 4 days at autogenous pressure. The extrudate was then washed with water adjusted to pH 10 using NH$_4$OH, dried overnight in a vacuum oven at 120° C., and calcined in air for 8 hours at 593° C. X-ray diffraction analysis identified the crystal phase as that of SSZ-35.

Example 16

This example shows the production of zeolite without extrusion. The product could be added to a binder and extruded or spray-dried conventionally.

To 150 grams of silica (Hi-Sil 233) were added 5.3 grams of $NaAlO_2$ and mixed for five minutes in a Baker-Perkins mixer. To this were added 95 grams of a 40 wt % aqueous solution of tetrapropylammonium hydroxide (TPAOH), 12 grams of a 50 wt % aqueous solution of NaOH and 50 grams of water, and the resulting mixture was mixed for three hours. Then 40 grams of water were added slowly until the mixture went to a paste. Then 12 grams of kaolin clay powder were added and mixing continued at 60° C. to reduce the volatiles level to 53 wt %. The mixture was then air-dried to yield a powder of 48 wt % volatiles. The molar ratio of $H_2O/SiO_2$ at this point was about 2.5. The powder was then placed in a Teflon bottle in a stainless steel pressure vessel and heated at 140° C. and autogenous pressure for two days. The resultting product was washed with water, dried overnight in a vacuum oven at 120° C., and calcined in air for three hours at 593° C. X-ray diffraction analysis showed the product to be nearly 100% ZSM-5. The average crystallite size by SEM was about 0.1 micron.

Example 17

This example shows the production of in-extrudate zeolite where $Al_2O_3$ is added as a binder material.

To 150 grams of Hi-Sil 233 were added 5.3 grams of $NaAOl_2$ in a Baker-Perkins mixer and mixed for five minutes. To this were added 95 grams of a 40 wt % aqueous solution of TPAOH, 12 grams of a 50 wt % aqueous solution of NaOH, and 50 grams of water, and the resulting mixture was mixed for three hours. Then 40 grams of acid-peptized and neutralized Catapal alumina (35% solids) were added and mixing continued for 15 minutes. Next, 30 grams of water were added to bring the mixture to a paste. Then, 8 grams of kaolin clay powder were added with mixing at 60° C. to bring the consistency of the mix to an extrudable form. The mix was extruded through a 1/12-inch die and air-dried to 46 wt % volatiles. The molar ratio of $H_2O/SiO_2$ was about 2.5. The extrudate was placed in a Teflon bottle in a stainless steel pressure vessel and heated at 140° C. and autogenous pressure for two days. The extrudate was then dried in a vacuum oven at 120° C. for six hours, and calcined i air at 593° C. for eight hours. X-ray diffraction showed the catalyst to contain about 80% ZSM-5.

Example 18

To 150 grams of silica (Hi-Sil 233) were added 10.5 grams of $Na_2B_2O_4.8H_2O$ and 1.0 grams of microcrystalline cellulose-and the resulting mixture was mixed for 10 minutes in a Baker-Perkins mixer. To this was added 103 grams of a 35 wt % aqueous solution of tetraethylammonium hydroxide (TEAOH), followed by 25 grams of water and 12 grams of a 50 wt % aqueous solution of NaOH and the resulting mixture was mixed for three hours. Then 30 g of water were slowly added to bring the mixture to a paste. Slow mixing continued with the mixer walls heated to about 60° C. to convert the mix to an extrudable mass. The mix was then extruded through a 1/12-inch die in a Carver press and placed on a screen to dry at room temperature to a volatiles content of 45 wt %. Molar ratios in the extrudate were as follows:

$TEA+/SiO_2=0.11$ $OH-/SiO_2=0.17$ $Na+/SiO_2=0.10$ $SiO_2/B_2O_3=56$ $H_2O/SiO_2=2.0$

The extrudate was placed in a Teflon bottle in a stainless steel pressure vessel and heated at 150° C. and autogenous pressure for four days. The extrudate was washed with water, dried overnight at 120° C. in a vacuum oven, and calcined in air at 593° C. for about eight hours. The product was identified as boron beta by x-ray diffraction analysis (see Table I). The average crystallite size was less than 0.2 microns as determined by scanning electron microscopy (SEM).

Example 19

To 150 grams of silica (Hi-Sil 233) in a Baker-Perkins mixer were added 10 grams of $Al(OH)_3$ (Reheis F2000, 53 wt % $Al_2O_3$, 47 wt % $H_2O$) and the resulting mixture was mixed for five minutes. To this were added 170 grams of a 1.15 molar solution of diisopropylimidazolium hydroxide, followed by 22 grams of a 50 wt % aqueous solution of KOH and the resulting mixture was mixed for 3.5 hours. To this were added 15 grams of water to bring the mix to a paste. Then 3.5 grams of kaolin clay powder were added, and slow mixing continued with the mixer walls heated to about 60° C. to convert the mix to an extrudable mass. The mix was then extruded through a 1/12-inch die in a Carver press and placed on a screen to dry at room temperature to a volatiles content of 45 wt %. Molar ratios in the extrudate were as follows:

$R+/SiO_2=0.086$ $OH-/SiO_2=0.17$ $M+/SiO_2=0.12$ $SiO_2/Al_2O_3=36$ $H_2O/SiO_2=2.3$

The extrudate was placed in a Teflon bottle in a stainless steel pressure vessel and heated at 170° C. and autogenous pressure for four days. The extrudate was washed with water, dried overnight at 120° C. in a vacuum oven, and calcined in air at 593° C. for about eight hours. The product was identified as ZSM-23-type by x-ray diffraction analysis.

TABLE I

| 2Θ | d spacing | Relative Intensity |
| --- | --- | --- |
| 7.150 | 12.3535 | 38.95 |
| 7.200 | 12.2678 | 40.60 |
| 7.250 | 12.1833 | 47.11 |
| 7.290 | 12.1165 | 47.78 |
| 7.614 | 11.6015 | 72.12 |
| 8.691 | 10.1657 | 11.69 |
| 13.477 | 6.5648 | 7.79 |
| 14.598 | 6.0633 | 7.23 |
| 20.560 | 4.3164 | 20.81 |
| 20.919 | 4.2431 | 31.43 |
| 21.661 | 4.0995 | 67.56 |
| 22.514 | 3.9460 | 100.00 |
| 23.010 | 3.8621 | 27.95 |
| 25.465 | 3.4950 | 7.71 |
| 27.234 | 3.2718 | 10.62 |
| 28.850 | 3.0922 | 8.41 |
| 29.749 | 3.0008 | 9.87 |
| 33.491 | 2.6735 | 5.96 |
| 35.947 | 2.4963 | 16.17 |

What is claimed is:

1. A method for preparing a crystalline zeolite, said method comprising:
   a. preparing a reaction mixture comprising at least one active source of a first oxide selected from the group consisting of an oxide of silicon, germanium or both, optionally at least one active source of a second oxide selected from the group consisting of an oxide of aluminum, boron, gallium, iron or a mixture thereof, an organic templating agent capable of forming said crystalline zeolite, and sufficient water to shape said mixture; and
   b. heating said reaction mixture at crystallization conditions and in the absence of an added external liquid phase for sufficient time to form a crystallized material containing crystals of said zeolite, wherein said zeolite crystals have a first oxide/second oxide molar ratio greater than 12.

2. The method according to claim 1 wherein said reaction mixture has a water/first oxide molar ratio during crystallization of no greater than about 5.

3. The method of claim 2 wherein said reaction mixture during crystallization has a water/first oxide molar ratio between about 1 and about 4.

4. The method according to claim 1 wherein said zeolite has a constraint index of greater than 1.

5. The method according to claim 1 wherein said zeolite crystals within said crystallized material have a crystallite size of less than 10 microns.

6. The method according to claim 5 wherein said zeolite crystals within said crystallized material have a crystallite size of less than 1.0 micron.

7. The method according to claim 1 wherein said crystallized material comprises greater than about 50 weight percent crystalline zeolite.

8. The method according to claim 7 wherein said crystallized material comprises greater than about 90 weight percent crystalline zeolite.

9. The method according to claim 1 wherein the reaction mixture contains no added seed crystals.

10. The method according to claim 1 wherein the crystalline zeolite is ZSM-5.

11. The method according to claim 1 wherein the crystalline zeolite is beta zeolite.

12. The method according to claim 1 wherein the crystalline zeolite is ZSM-12.

13. The method according to claim 1 wherein the crystalline zeolite is silicalite.

14. The method according to claim 1 wherein the crystalline zeolite is SSZ-35.

15. The method according to claim 1 wherein the crystalline zeolite is ZSM-23.

16. The method according to claim 1 wherein the crystalline zeolite is SSZ-32.

17. The method according to claim 1 wherein the crystalline zeolite is boron beta.

18. The method according to claim 1 wherein said reaction mixture has the following molar composition ranges:

$SiO_2/Al_2O_3 = 12-\infty$ $M^+/SiO_2 = 0-1$ $R/SiO_2 = 0.01-0.5$ $OH^-/SiO_2 = 0.05-0.4$ $H_2O/SiO_2 = 0.5-5$ wherein $M^+$ is a alkali cation and R is a templating agent.

19. The method according to claim 18 wherein said reaction mixture has the following molar composition ranges:

$SiO_2/Al_2O_3 = 12-\infty$ $M^+/SiO_2 = 0.03-0.5$ $R/SiO_2 = 0.01-0.3$ $OH^-/SiO_2 = 0.05-0.3$ $H2O/SiO_2 = 1-4$ wherein $M^+$ is a alkali cation and R is a templating agent.

20. The method according to claim 1 wherein said reaction mixture comprises at least one active source of alumina.

21. The method according to claim 20 wherein said zeolite crystals formed in the step of heating said reaction mixture have a silica/alumina molar ratio in the range of 12 to about 5000.

22. The method according to claim 1 wherein said reaction mixture further comprises at least one active source of a Group VIII metal.

23. The method according to claim 22 wherein said Group VIII metal is selected from platinum, palladium and a combination thereof.

24. The crystalline zeolite prepared by the method according to claim 23.

25. A method for preparing a shaped crystalline zeolite, said method comprising:
   a. preparing a reaction mixture comprising at least one active source of a first oxide selected from the group consisting of an oxide of silicon, germanium or both, optionally at least one active source of a second oxide selected from the group consisting of an oxide of aluminum, boron, gallium, iron or a mixture thereof, an organic templating agent capable of forming said crystalline zeolite, and sufficient water to shape said mixture;
   b. forming said reaction mixture into shaped particles; and
   c. heating said shaped particles at crystallization conditions and in the absence of an added external liquid phase for sufficient time to form crystals of said zeolite within said shaped particles, wherein said zeolite crystals have a first oxide/second oxide molar ratio greater than 12.

26. The method according to claim 25 where said shaped particles have a water/first oxide molar ratio during crystallization of no greater than about 5.

27. The method of claim 26 wherein said shaped particles during crystallization have a water/first oxide mole ratio between about 1 and about 4.

28. The method according to claim 25 wherein said zeolite has a constraint index of greater than 1.

29. The method according to claim 25 wherein said zeolite crystals have a crystallite size of less than 10 microns.

30. The method according to claim 29 wherein said zeolite crystals have a crystallite size of less than 1.0 micron.

31. The method according to claim 25 wherein said shaped particles containing said crystallized zeolite comprise greater than about 50 weight percent crystalline zeolite.

32. The method according to claim 31 wherein said shaped particles containing said crystallized zeolite comprise greater than about 90 weight percent crystalline zeolite.

33. The method according to claim 25 wherein the reaction mixture contains no added seed crystals.

34. The method according to claim 25 wherein said crystalline zeolite is ZSM-5.

35. The method according to claim 25 wherein said crystalline zeolite is beta zeolite.

36. The method according to claim 25 wherein said crystalline zeolite is ZSM-12.

37. The method according to claim 25 wherein said crystalline zeolite is silicalite.

38. The method according to claim 25 wherein said crystalline zeolite is SSZ-35.

39. The method according to claim 25 wherein said crystalline zeolite is ZSM-23.

40. The method according to claim 25 wherein said crystalline zeolite is SSZ-32.

41. The method according to claim 25 wherein said crystalline zeolite is boron beta.

42. The method according to claim 25 wherein said reaction mixture has the following molar composition ranges:

$SiO_2/Al_2O_3 = 12-\infty$ $M^+/SiO_2 = 0-1$ $R/SiO_2 = 0.01-0.5$ $OH^-/SiO_2 = 0.05-0.4$ $H_2O/SiO_2 = 0.5-5$ wherein $M^+$ is a alkali metal cation and R is a templating agent.

43. The method according to claim 42 wherein said reaction mixture has the following molar composition ranges:

$SiO_2/Al_2O_3 = 12-\infty$ $M^+/SiO_2 = 0.03-0.5$ $R/SiO_2 = 0.01-0.3$ $OH^-/SiO_2 = 0.05-0.3$ $H_2O/SiO_2 = 1-4$ wherein $M^+$ is a alkali metal cation and R is a templating agent.

44. The method according to claim 25 wherein the shaped crystalline zeolite is a spherical or cylindrical particle having a cross sectional diameter between about 1/64 inch and about 1/2 inch.

45. The method according to claim 42 wherein the shaped crystalline zeolite is a spherical or cylindrical particle having a cross sectional diameter between about 1/32 inch and about 1/4 inch in diameter.

46. The method according to claim 25 wherein said reaction mixture comprises at least one active source of alumina wherein the silica/alumina molar ratio in the reaction mixture is in the range of 12 to about 5000.

47. The method according to claim 25 wherein said zeolite crystals formed in the step of heating said reaction mixture have a silica/alumina molar ratio in the range of 12 to about 5000.

48. The method according to claim 25 wherein said reaction mixture further comprises at least one active source of a Group VIII metal.

49. The method according to claim 48 wherein said Group VIII metal is selected from platinum, palladium and a combination thereof.

50. The crystalline zeolite prepared by the method according to claim 49.

51. The method to claim 1 wherein said reaction mixture has a composition, in terms of mole ratios, falling within the following ranges:

$YO_2/W_2O_3$ 12–∞

$M^+/YO_2$ 0–1

$R/YO_2$ 0–0.5

$OH/YO_2$ 0.01–0.5

$H_2O/YO_2$ 0.5–5 wherein Y is silicon, germanium or both, W is aluminum, boron, gallium, iron, or a mixture thereof, $M^+$ is an alkali metal ion, an R is a templating agent.

52. The method according to claim 51 wherein said reaction mixture has a composition, in terms of mole ratios, falling within the following ranges:

$YO_2W_2O_3$ 12–∞

$M^+/YO_2$ 0.04–0.7

$R/YO_2$ 0.01–0.3

$OH/YO_2$ 0.05–0.3

$H_2O/YO_2$ 1–4 wherein Y is silicon, germanium or both, W is aluminum, boron, gallium, iron, or a mixture thereof, $M^+$ is an alkali metal ion, and R is a templating agent.

* * * * *